United States Patent
Hommeltoft et al.

(10) Patent No.: US 8,729,329 B2
(45) Date of Patent: May 20, 2014

(54) SUPPORTED LIQUID PHASE IONIC LIQUID CATALYST PROCESS

(75) Inventors: Sven Ivar Hommeltoft, Pleasant Hill, CA (US); Zhen Zhou, Emeryville, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 225 days.

(21) Appl. No.: 12/824,854

(22) Filed: Jun. 28, 2010

(65) Prior Publication Data
US 2011/0319695 A1    Dec. 29, 2011

(51) Int. Cl.
*C07C 2/58*    (2006.01)
(52) U.S. Cl.
USPC ............... 585/724; 585/721; 585/728
(58) Field of Classification Search
USPC ............ 585/724, 721, 728, 732, 730, 709
See application file for complete search history.

(56) References Cited

U.S. PATENT DOCUMENTS

| | | | | |
|---|---|---|---|---|
| 2,949,494 | A * | 8/1960 | Putney | 585/715 |
| 3,116,346 | A | 12/1963 | Van Dyke | |
| 4,011,166 | A | 3/1977 | Schenach | |
| 4,139,573 | A * | 2/1979 | Carson | 585/701 |
| 4,990,709 | A | 2/1991 | Wu | |
| 5,208,403 | A | 5/1993 | Buchanan et al. | |
| 6,395,948 | B1 | 5/2002 | Hope et al. | |
| 7,256,152 | B2 | 8/2007 | Olivier-Bourbigou et al. | |
| 7,432,408 | B2 * | 10/2008 | Timken et al. | 585/709 |
| 2002/0169071 | A1 * | 11/2002 | Sauvage et al. | 502/150 |
| 2004/0035293 | A1 | 2/2004 | Davis, Jr. | |
| 2005/0033102 | A1 * | 2/2005 | Randolph et al. | 585/708 |
| 2006/0287521 | A1 | 12/2006 | Davis, Jr. | |
| 2007/0142690 | A1 * | 6/2007 | Elomari | 585/727 |
| 2007/0225538 | A1 | 9/2007 | Elomari | |
| 2007/0295647 | A1 | 12/2007 | Brownscombe et al. | |
| 2008/0142412 | A1 | 6/2008 | Driver et al. | |
| 2009/0107032 | A1 | 4/2009 | Lacheen et al. | |
| 2009/0170687 | A1 | 7/2009 | Luo et al. | |

(Continued)

FOREIGN PATENT DOCUMENTS

| | | |
|---|---|---|
| WO | WO2005002726 | 1/2005 |
| WO | WO2007124397 | 11/2007 |

OTHER PUBLICATIONS

Hommeltoft, Applied Catalysis A: General 221 (2001) 421-428.

(Continued)

*Primary Examiner* — In Suk Bullock
*Assistant Examiner* — Sharon Pregler
(74) *Attorney, Agent, or Firm* — Susan M. Abernathy

(57) ABSTRACT

A process, comprising:
  a) introducing an acidic ionic liquid to a reactor comprising a solid support;
  b) feeding to the reactor a feed stream comprising a Brønsted acid and a hydrocarbon mixture comprising:
     i. at least one alkylatable hydrocarbon, and
     ii. at least one alkylating agent; and
  c) collecting one or more liquid hydrocarbon products in an effluent from the reactor, wherein the one or more liquid hydrocarbon products are oligomer products, alkylate products, or mixtures thereof, made from the alkylatable hydrocarbon. Also, a process, comprising:
  a) introducing an acidic ionic liquid to a reactor comprising a solid support;
  b) feeding to the reactor a feed stream comprising a Brønsted acid and a hydrocarbon mixture;
  c) cooling the reactor by evaporating a volatile hydrocarbon from a reaction zone in the reactor; and
  d) collecting one or more liquid hydrocarbon products made from the hydrocarbon mixture.

32 Claims, 2 Drawing Sheets

(56) References Cited

U.S. PATENT DOCUMENTS

| | | |
|---|---|---|
| 2009/0176956 A1 | 7/2009 | Grinstaff et al. |
| 2009/0306444 A1 | 12/2009 | Elomari et al. |
| 2010/0025292 A1 | 2/2010 | Hommeltoft et al. |
| 2010/0025296 A1 | 2/2010 | Hommeltoft |
| 2010/0065476 A1 | 3/2010 | Hommeltoft et al. |
| 2010/0094072 A1 | 4/2010 | Randolph et al. |
| 2010/0298620 A1 | 11/2010 | Hommeltoft |

OTHER PUBLICATIONS

J. Am. Chem. Soc. 2002, 124(44), 12932-12933; ionic liquids have been used on solid support for homogeneous hydroformylation.

PCT.US2011/031697, mailing date Feb. 17, 2012, 11 pages.

T-7680, PCT/US2011/031697 form PCT/IB/326 "Notification Concerning Transmittal of International Preliminary Report on Patentability (Chapter 1 of the Patent Cooperation Treaty)", mail date Jan. 10, 2013, 7 pages.

\* cited by examiner

SUPPORTED LIQUID PHASE IONIC LIQUID CATALYST PROCESS

This application is related to two co-filed patent applications, titled "PROCESS TO CONTROL PRODUCT SELECTIVITY" and "SUPPORTED IONIC LIQUID REACTOR," herein incorporated in their entireties.

TECHNICAL FIELD

This application is directed to processes for producing liquid hydrocarbon products with an ionic liquid in a reactor comprising a solid support.

SUMMARY

This application provides a process for producing liquid hydrocarbon products, comprising:
  a) introducing an acidic ionic liquid to a reactor comprising a solid support;
  b) feeding to the reactor a feed stream comprising a Brønsted acid and a hydrocarbon mixture comprising:
    i. at least one alkylatable hydrocarbon, and
    ii. at least one alkylating agent; and
  c) collecting one or more liquid hydrocarbon products in an effluent from the reactor, wherein the one or more liquid hydrocarbon products are oligomer products, alkylate products, or mixtures thereof, made from the alkylatable hydrocarbon.

This application also provides a process for producing liquid hydrocarbon products, comprising:
  a) introducing an acidic ionic liquid to a reactor comprising a solid support;
  b) feeding to the reactor a feed stream comprising a Brønsted acid and a hydrocarbon mixture;
  c) cooling the reactor by evaporating a volatile hydrocarbon from a reaction zone in the reactor; and
  d) collecting one or more liquid hydrocarbon products in an effluent from the reactor, wherein the one or more liquid hydrocarbon products are oligomer products, alkylate products, or mixtures thereof, made from the hydrocarbon mixture.

DETAILED DESCRIPTION

Figure 1:
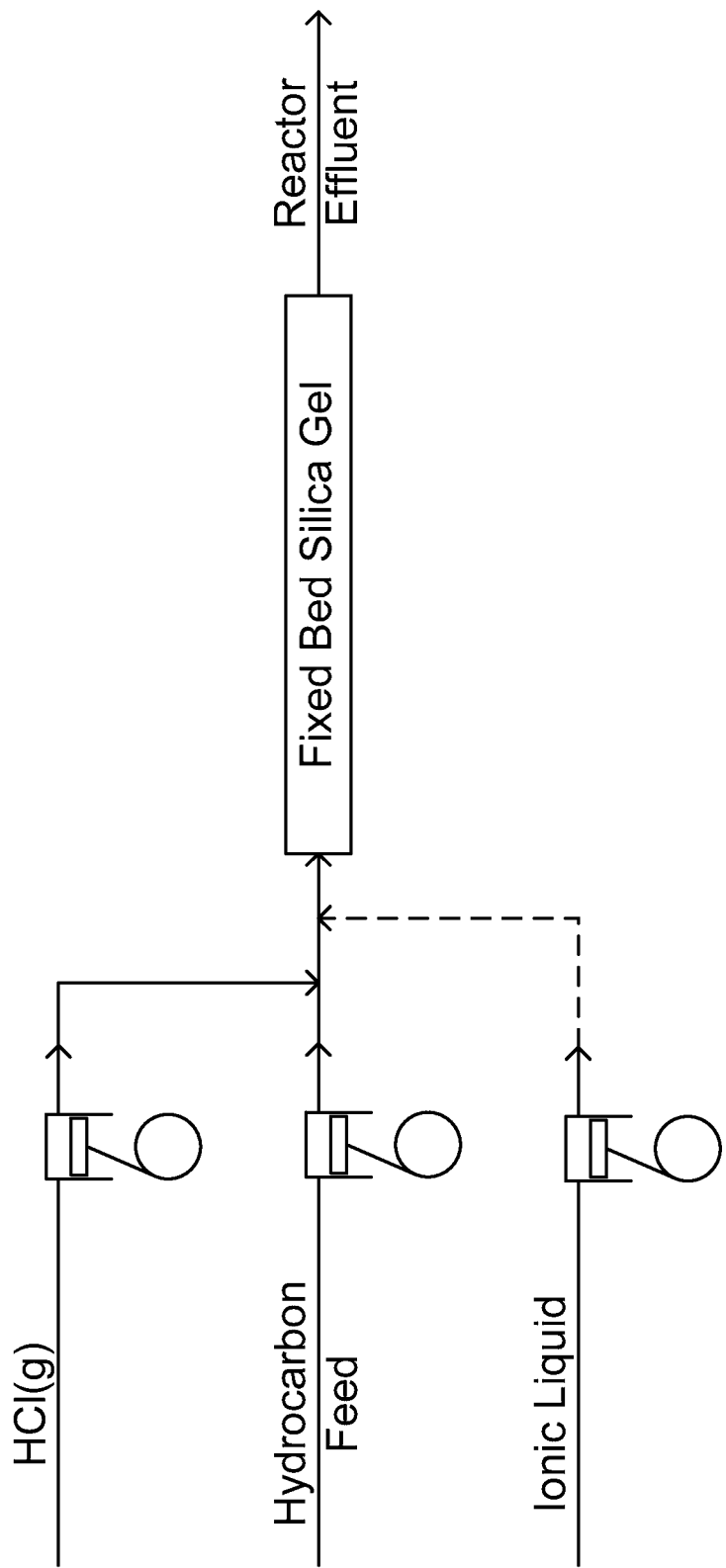
FIG. 1 is a process flow diagram of the experimental setup used for Example 1 in this disclosure.

This process is used to produce liquid hydrocarbons. Examples of liquid hydrocarbons that can be made by the process are alkylate gasoline blending components, naphtha, heavy naphtha, jet fuel, diesel, base oil, and bright stock.

The solid support can be any solid that supports the acidic ionic liquid. Examples of solid supports include silica, alumina, titania, zirconia, thoria, boria, niobium oxide, tin oxide, and mixtures thereof. In another embodiment, the solid support can comprise polymer resins with pyridine groups, amine groups, or other basic groups; or porous forms of carbon, including forms of activated carbon. For example, the solid support can be protonated forms of polyvinyl pyridine crosslinked with divinyl benzene and/or polystyrene amines.

In one embodiment, the solid support is able to form an adduct with the acidic ionic liquid and the solid support does not react or disintegrate under operating conditions in the reactor.

The solid support, for example, can be in the shape of pellets, multi-channel cylinders, a honeycomb, a helix, and a variety of polygonal arrangements typical for fixed bed reactors. In one embodiment, the solid support is a porous particulate. A porous particulate can have pores up to 200 Å, such as in the range of 20 to 150 Å, or 30 to 100 Å. In another embodiment, the solid support comprises a particulate having a diameter in the longest direction from 25 to 3000 μm.

In one embodiment, the porous particulate is placed in a fixed bed and a pore volume in the reactor is greater than 25 vol % of a total volume of the reactor. In other embodiments the pore volume is from greater than 25 vol % up to 70 vol %, from 30 to 50 vol %, from 35 to 45 vol %, or approximately 40 vol % of the total volume of the reactor.

The acidic ionic liquid is composed of at least two components which form a complex. The acidic ionic liquid comprises a first component and a second component. The first component of the acidic ionic liquid can comprise a Lewis Acid. The Lewis acid can be a metal halide compound selected from components such as Lewis Acidic compounds of Group 13 metals, including aluminum halides, alkyl aluminum halide, gallium halide, and alkyl gallium halide. Other Lewis Acidic compounds, such as Group 3, 4, and 5 metal halides, in addition to those of Group 13 metals, can also be used. Other specific examples include $ZrCl_4$, $HfCl_4$, $NbCl_5$, $TaCl_5$, $ScCl_3$, $YCl_3$, and mixtures thereof. The periodic table by the International Union of Pure and Applied Chemistry (IUPAC), version date 22 Jun. 2007, is used for defining the Groups 3, 4, 5, and 13 metals. In one embodiment the first component is aluminum halide or alkyl aluminum halide. For example, aluminum trichloride can be the first component of the acidic ionic liquid.

The second component making up the acidic ionic liquid is an organic salt or mixture of salts. These salts can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^{--}$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the acidic ionic liquid is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the acidic ionic liquid can be an acidic haloaluminate ionic liquid, such as an alkyl substituted pyridinium chloroaluminate or an alkyl substituted imidazolium chloroaluminate of the general formulas A and B, respectively.

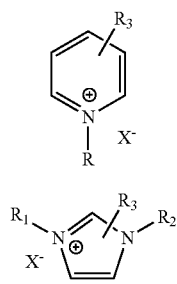

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same. In one embodiment the acidic ionic liquid is N-butylpyridinium chloroaluminate.

In one embodiment acidic ionic liquid comprises a cation selected from the group of an alkyl-pyridinium, an alkyl-imidazolium, or a mixture thereof. In another embodiment the acidic ionic liquid can have the general formula RR'R"N $H^+Al_2Cl_7^-$, wherein N is a nitrogen containing group, and wherein RR' and R" are alkyl groups containing 1 to 12 carbons, and where RR' and R" may or may not be the same.

The presence of the first component should give the acidic ionic liquid a Lewis acidic character. In one embodiment the ionic liquid catalyst includes strongly Lewis acidic anions, such as $Al_2Cl_7^-$. $Al_2Cl_7^-$, for example, is a strongly Lewis acidic anion, while $AlCl_4^-$ is not. Generally, the greater the mole ratio of the first component to the second component, the greater is the acidity of the acidic ionic liquid catalyst.

In one embodiment, the acidic ionic liquid comprises less than one wt %, less than 0.5 wt %, or no, silyl-containing groups. Silyl-containing groups comprise $H_3Si$— or hydrocarbyl derivatives thereof, e.g. $R_3Si$—. Examples of silyl-containing groups are siloxanes and silanes. Siloxanes, for example, are typically not stable in very strongly acidic media.

In one embodiment the acidic ionic liquid is a catalyst for an alkylation, an oligomerization, or a combination thereof. In another embodiment the acidic ionic liquid serves as an adsorbent for the Brønsted acid, and the Brønsted acid is a catalyst for an alkylation, an oligomerization, or a combination thereof. In yet another embodiment, the acidic ionic liquid serves as both an adsorbent and a promoter for the Brønsted acid, wherein the Brønsted acid is a catalyst for an alkylation, an oligomerization, or a combination thereof. An adsorbent is a substance, usually porous, that allows the molecules of a gas or liquid to adhere to its large surface area. A promoter is a substance that will accelerate the effect of a catalyst on a reaction.

A Brønsted acid is any substance that can donate an $H^+$ ion to a base. Brønsted acids are $H^+$-ion or proton donors. Examples of Brønsted acids are HCl, HBr, HI, HF, sulfuric acid, $+NH_4$, $NH_3$, $CH_3CO_2H$, $H—CH_2COCH_3$, $H—C\equiv CH$, $H—CH_3$, and mixtures thereof.

In one embodiment the solid support is placed in a fixed bed or a fluidized bed. A fixed bed has a solid support held in a stable position in a reactor. A fluidized bed has solid particles that are at least partially suspended in a reactor such that the solid particles are substantially free to move about within the reactor, as driven by the flow of a feed stream through the reactor. In one aspect, the solid support is placed in the fixed bed or fluidized bed and the feed stream is introduced at one end of the reactor and withdrawn at the opposite end of the reactor. In one embodiment the end where the feed stream is introduced is the top and the opposite end is the bottom. There can be a grid at the opposite end of the reactor to hold the solid support inside the reactor, but to allow the fluid products to pass through.

An alkylating agent is a chemical that can add alkyl groups (for example, ethyl or methyl groups) to another molecule. Examples of alkylating agents are cyclopropane, alkyl halides, aliphatic alcohols, alkyl ethers, alkyl esters, olefins, and mixtures thereof. In one embodiment the alkylating agent comprises an olefin. The olefin can be a single olefin, or a mixture of olefins. The olefin can be an alpha olefin, an internal olefin, or a combination thereof. In one embodiment the olefin comprises a $C_2$-$C_{12}$ olefin. In another embodiment the olefin comprises $C_2$-$C_{25}$, or $C_{12}$-$C_{25}$ olefins. The olefin can be made by a number of processes known to those skilled in the art, including thermal cracking, catalytic dehydrogenation, catalytic cracking (e.g., fluid catalytic cracking (FCC)), Fischer-Tropsch synthesis, oxidative chlorination of methane, dehydration of alcohols, and oligomerization of ethylene. In one embodiment the alkylating agent comprises mixed butenes, mixed pentenes, or a combination thereof. These alkylating agents can be produced, for example in a FCC unit.

In one embodiment, the alkylating agent comprises at least 15 wt % 1-butene and the one or more liquid hydrocarbons comprise a bright stock. By increasing the amount of alpha olefin, e.g., 1-butene, in the alkylating agent, the wt % bright stock that is produced can be increased. The wt % bright stock, for example, can be adjusted from 0.1 wt % to 20 wt % by adjusting the amount of alpha olefin in the alkylating agent.

The alkylatable hydrocarbon is a hydrocarbon that is capable of having an alkyl group added to or substituted into it. Examples of these hydrocarbons are olefins, isoparaffins, branched naphthenes, aromatic hydrocarbons, and mixtures thereof. In one embodiment the alkylatable hydrocarbon is a $C_4$-$C_{25}$ isoparaffin. In some embodiments the alkylatable hydrocarbon comprises $C_{12}$-$C_{25}$ isoparaffin or olefin. These heavier types of alkylatable hydrocarbons are available from several sources, including from Fischer-Tropsch condensate.

In one embodiment the alkylatable hydrocarbon comprises an isoparaffin and the alkylating agent comprises an olefin. For example, in one embodiment the hydrocarbon stream comprises a $C_4$-$C_{25}$ isoparaffin and a $C_2$-$C_{12}$ olefin.

In another embodiment the at least one alkylatable hydrocarbon and the at least one alkylating agent both comprise olefins. This can be the case, for example, when the one or more liquid hydrocarbon products are oligomer products. Oligomer products are polymers having only a few monomer units such as a dimer, trimer, tetramer, etc., or their mixtures.

Gasoline blending components can be blended into gasoline or used directly as gasoline. Examples of gasoline blending components are naphtha and heavy naphtha. In the context of this disclosure, naphtha has a boiling range distribution less than 130° C. and heavy naphtha has a boiling range distribution from 130 to 200° C. In one embodiment, the gasoline blending component has a high octane number. Examples of high octane numbers are 82 or higher, 85 or higher, 90 or higher, and 95 or higher. Different methods are used for calculating octane numbers of fuels or fuel blend components. The Research-method octane number (RON) is determined using ASTM D 2699-07a. RON employs the standard Cooperative Fuel Research (CFR) knock-test engine. Additionally, the Research-method octane number can be calculated [RON (GC)] from gas chromatography boiling range distribution data. The RON (GC) calculation is described in the publication, Anderson, P. C., Sharkey, J. M., and Walsh, R. P., "Journal Institute of Petroleum", 58 (560), 83 (1972). Another measure of the octane number of a fuel is the motor octane number (MON). MON correlates with commercial automotive spark-ignition engine antiknock performance under severe conditions of operation. MON can be determined by ASTM D 2700-09.

In one embodiment the one or more liquid hydrocarbons comprise a gasoline blending component, a middle distillate, a lubricant, or a mixture thereof. A "middle distillate" is a hydrocarbon product having a boiling range between 250° F. to 735° F. (121° C. to 391° C.). The term "middle distillate" includes the diesel, heating oil, jet fuel, and kerosene boiling range fractions. It can also include a portion of naphtha or light oil. In the context of this disclosure, a "lubricant" is a hydrocarbon boiling in the range of about 650° F. (343 degree Celsius) and higher. Lubricants can be blended with additives and used, for example, as diluents for the additives or in finished lubricants.

The test methods used for boiling range distributions of the products in this disclosure are ASTM D 2887-06a and ASTM D 6352-04. The test method is referred to herein as "SIMDIST". The boiling range distribution determination by distillation is simulated by the use of gas chromatography. The boiling range distributions obtained by this test method are essentially equivalent to those obtained by true boiling point (TBP) distillation (see ASTM Test Method D 2892), but are not equivalent to results from low efficiency distillations such as those obtained with ASTM Test Methods D 86 or D 1160.

In one embodiment, a fresh acidic ionic liquid is added continuously to the reactor and a passivated acidic ionic liquid is withdrawn continuously from the reactor. Acidic ionic liquid can be passivated by lowering its acidity. This can happen, for example, by complexing with conjunct polymers that form as a byproduct during an alkylation reaction. By continuously adding fresh acidic ionic liquid to the reactor the catalyst activity can be controlled. The passivated acidic ionic liquid catalyst can be regenerated in full or in part, and recycled back to the reactor. Because the acidic ionic liquid is in the reactor with a solid support, the average residence time for the acidic ionic liquid in the reactor can be different than the average residence time for the hydrocarbon mixture in the reactor. This is different than in earlier reactor designs where the acidic ionic liquid catalyst was mixed and agitated with the hydrocarbon mixture, forming an emulsion.

In one embodiment, the acidic ionic liquid catalyst and the one or more liquid hydrocarbons do not form an emulsion. One technical advantage of the process can thus be that the phase separation of the acidic ionic liquid from the liquid hydrocarbons can be less difficult, and this is especially helpful in embodiments where lubricants and/or bright stock are being produced. Bright stock is a lubricant having a kinematic viscosity above 180 $mm^2/s$ at 40° C.

In one embodiment, the difference between the average residence time for the hydrocarbon mixture and the average residence time for the acidic ionic liquid in the reactor is at least 30 seconds, at least 1 minute, at least 2 minutes, at least 5 minutes, or at least 8 minutes. The flow of the acidic ionic liquid during the introducing of the acidic ionic liquid to the reactor and the flow of the feed stream comprising the hydrocarbon mixture can be varied independently to optimize the process.

In one embodiment the reactor is operated adiabatically. During an adiabatic process, any temperature changes are due to internal system fluctuations, and there is no externally supplied heating or cooling. Operating in this mode can provide significant equipment savings and reductions in process complexity. One way that temperature in the reactor can be maintained in a suitable range is by having a volatile hydrocarbon from a reaction zone in the reactor evaporate to cool the reactor. By having a volatile hydrocarbon from the reaction zone evaporate to cool the reactor the temperature in the reactor can be maintained within 10° C., within 5° C., or within 1° C. In one embodiment, a volatile hydrocarbon from the reaction zone in the reactor evaporates to cool the reactor and the reactor is maintained at a temperature from 25 to 60° C., such as 30 to 50° C., 35 to 45° C., or 35 to 40° C. This means of cooling the reactor is highly scalable, and can be used on any reactor size from a small micro-unit reactor in a research lab, to a reactor in a pilot plant, and up to a full size reactor in a large refinery operation. Examples of volatile hydrocarbons from the reaction zone that can provide cooling include $C_6^-$ normal alkanes, isoparaffins, and olefins. Specific examples are ethylene, ethane, propane, n-butane, isobutane, isobutene, and mixtures thereof.

In other embodiments, cooling can be provided by a heat transfer fluid or coolant. In some embodiments the reactor is cooled by transferring heat through a wall of the reactor.

In one embodiment, greater than 95 wt % of the alkylating agent is converted. In other embodiments, the wt % of the alkylating agent that is converted is greater than 97 wt %, greater than 98 wt %, greater than 99 wt %, or 100 wt %. High levels of conversion are desired so to most efficiently use the alkylating agent and to not require recapturing it or recycling it from the effluent.

In one embodiment, the feed rate of the alkylating agent to the reactor is higher than is what is typically used in either continuously stirred tank reactors or nozzle loop reactors. For example, the feed rate of the alkylating agent can be at least 1.2 LHSV, at least two LHSV, at least three LHSV, up to as high as 50 LHSV. This high feed rate means that the volume of the reactor to convert a given amount of alkylating agent is reduced. The reduction in the reactor volume can be inversely proportional to the feed rate. LHSV is the linear hourly space velocity, defined as the ratio of the hourly volume of oil processed to the volume of catalyst. It is generally expressed as v/v/hr or $hr^{-1}$.

The quality of the one or more liquid hydrocarbons produced by the process can be exceptional. For example the one or more liquid hydrocarbons that are heavy naphtha or jet fuel can have a high smoke point, such as 30 mm or higher, 35 mm or higher, or 40 mm or higher. Smoke point can be determined by ASTM D 1322-08. In the context of this disclosure, heavy naphtha has a boiling range from 130-200° C., and jet fuel has a boiling range from 200-290° C. In another example, the one or more liquid hydrocarbons comprise a bright stock. The bright stock can have a high viscosity index (VI), such as 75 or higher, 80 or higher, 90 or higher, 100 or higher, 110 or higher, or 120 or higher. In one embodiment the one or more liquid hydrocarbons comprise a bright stock having a kinematic viscosity at 100° C. of 200 $mm^2/s$ or higher and a VI of 80 or higher. VI is determined by ASTM D 2270-04.

In one embodiment, the one or more liquid hydrocarbons in the effluent from the reactor comprise at least 2 wt % hydrocarbons with a boiling point greater than 500° C. In other embodiments the one or more liquid hydrocarbons in the effluent from the reactor comprise at least 3 wt %, at least 4 wt %, at least 5 wt %, at least 6 wt %, or at least 8 wt % hydrocarbons with a boiling point greater than 500° C. In one embodiment, the hydrocarbons with a boiling point greater than 500° C. are 60 wt % or less.

In one embodiment, the one or more liquid hydrocarbons comprise: a) at least 5 wt % hydrocarbons with a boiling point less than 130° C. and having a RON of 90 or higher, and b) a bright stock with a VI greater than 100. In another embodiment, the one or more liquid hydrocarbons comprise: a) a lubricant having a kinematic viscosity of 180 mm$^2$/s or less at 40° C. and a VI greater than 15, and b) a bright stock with a VI greater than 100.

EXAMPLES

Example 1

A reactor was dense-packed with a fixed bed of silica gel (4.0 g/9.5 ml DAVISIL™ silica gel, Type 60Å, 35-60 mesh, 250-500 μm particle size). DAVISIL® is a registered trademark of W.R. Grace & Co. Prior to packing the reactor, the silica gel was dried in a stream of nitrogen at 200° C. The reactor was a 50 cm ¼" ID perfluoroalkoxy (PFA) tube. Small patches of glass wool were applied at each end of the PFA reactor tube to keep the silica gel in place. The volume of the fixed bed in the PFA reactor tube was about 15 ml. This reactor was part of a laboratory process unit, which is illustrated in FIG. 1.

Three feed streams were fed to the PFA reactor tube. The tests done using the PFA reactor tube were all done at ambient pressure and at ambient inlet temperature. The first feed stream was gaseous HCL, which was pumped to the PFA reactor tube using an FMI piston pump operated with an inlet pressure of about 2-3 psi above ambient. The second feed stream was a hydrocarbon feed comprising 2-pentene and isopentane as reactants. The second feed stream was pumped to the PFA reactor tube using another FMI piston pump. The third feed stream was N-butylpyridinium chloroaluminate ($C_5H_5C_4H_9Al_2Cl_7$) ionic liquid catalyst. The third feed stream was pumped to the PFA reactor tube using a peristaltic pump.

Before introduction of the 2-pentene in the second feed stream into the PFA reactor tube, the PFA reactor tube was filled with isopentane flowing at a rate of 5 ml/min. Subsequently, the ionic liquid catalyst was slowly added to the isopentane flowing into the PFA reactor tube until about half of the PFA reactor tube volume was loaded with ionic liquid catalyst. The loading of the ionic liquid catalyst was visible from the outside of the PFA reactor tube because the silica gel turned yellow brown as it became loaded with the ionic liquid catalyst.

Once visual inspection showed that half of the PFA reactor tube was loaded with ionic liquid catalyst, flow of ionic liquid catalyst was stopped while isopentane flow was continued for an additional 4 minutes to allow the ionic liquid catalyst to settle into the silica gel support. It is believed that when the PFA reactor tube was loaded that the ionic liquid catalyst filled the pore volume of the silica gel, wetted the surface of the particles, and left a void largely open to hydrocarbon flow. The volume of ionic liquid catalyst in the PFA reactor tube was estimated to be 4 ml.

After the ionic liquid catalyst had settled into the silica gel support, the hydrocarbon feed was changed to 5 ml/min 2% 2-pentene in isopentane (approximately 0.90 mmole olefin/min). HCl was also added to the PFA reactor tube at a flow of about 1 Nml/min (0.04 mmole/min).

Liquid GC samples of hydrocarbons were collected from the PFA reactor tube effluent. The samples of hydrocarbons were each washed with water immediately after collection. The liquid GC samples were taken every 5 minutes for the first 20 minutes after the hydrocarbon feed was changed. All these samples showed 100% olefin conversion, yielding an alkylate product rich in iso-$C_{10}$ boiling range material.

After the first 20 minutes, the HCl flow was stopped and sampling of hydrocarbons continued to be taken every 5 minutes for the next 30 minutes. Again, all the samples showed 100% olefin conversion. The hydrocarbon feed was changed a second time to 5 ml/min 5 wt % 2-pentene in isopentane (approximately 2.2 mmoles olefin/min). A liquid GC sample of hydrocarbons collected from the PFA reactor tube effluent 8 minutes after the hydrocarbon feed was changed a second time showed 100% olefin conversion. A liquid GC sample of hydrocarbons collected from the PFA reactor tube effluent 15 minutes after the hydrocarbon feed was changed a second time showed 99.7% olefin conversion. A liquid GC sample of hydrocarbons collected from the PFA reactor tube effluent 20 minutes after the hydrocarbon feed was changed a second time showed only 72% olefin conversion.

When the liquid GC sample of hydrocarbons collected from the PFA reactor tube showed only 72% olefin conversion the HCl flow was started again at a flow of about 1 Nml/min. 10 minutes after the restarting of the HCl the liquid GC sample of hydrocarbons collected from the PFA reactor tube effluent showed 99.9% olefin conversion.

While feeding the 5 wt % 2-pentene a substantial part of the isopentane evaporated, causing a gas flow out of the PFA reactor tube. This gas flow was caused by the heat of reaction in the PFA reactor tube. The gas flow was countered by submerging the PFA reactor tube in cold water.

Example 2

Figure 2:
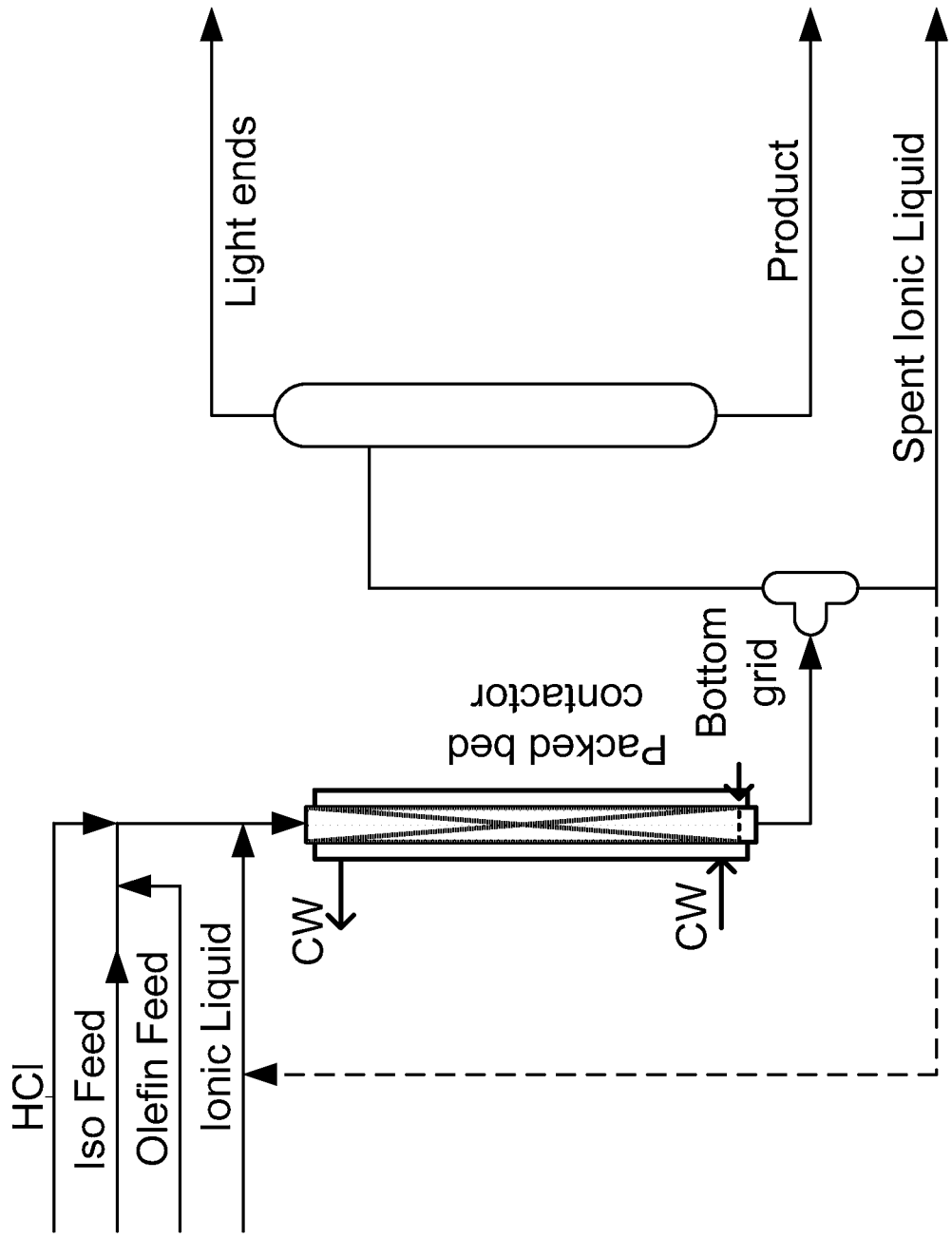
FIG. 2 is a process flow diagram of the experimental setup used for Example 2 in this disclosure.

4.0 g/9.5 ml DAVISIL™ Type 60Å, 35-60 mesh, silica gel was dried in a stream of nitrogen at 180° C. The dried silica gel was loaded into an 8" long, ⅜" OD reactor tube (packed bed contactor) with a cooling mantle for cooling brine. Once loaded into the reactor tube, the silica gel had a volume of roughly 1 ml/g. This packed bed contactor was part of a laboratory process unit, which is illustrated in FIG. 2.

A series of five experiments were conducted, where a combined feed stream comprising pure isoparaffin (Iso Feed) and different olefin feeds were fed to the packed bed contactor. The olefin feeds were passed through a mol sieve drier, but had no further purification, diene saturation or isomerization prior to being fed to the packed bed contactor. The combined feed stream was mixed with a small amount of HCl and fed to the top of the packed fed contactor along with a flow of ionic liquid. The ionic liquid was N-butylpyridinium chloroaluminate ($C_5H_5C_4H_9Al_2Cl_7$) ionic liquid catalyst. The volume distributions in the packed bed contactor were estimated to be about 40 vol % pore volume (most of which was filled by ionic liquid during operation), about 40 vol % void (part of which was filled by ionic liquid during operation), and 20 vol % $SiO_2$ framework.

The different olefin feeds that were tested included mixed FCC butenes and mixed FCC pentenes. The mixed FCC butenes were combined with isobutane and the mixed FCC pentenes were combined with isopentane. The mixed FCC butenes comprised approximately 20 wt % to 25 wt % 1-butene.

An effluent was collected at the bottom of the packed bed contactor during each run. The effluent was depressurized, the ionic liquid phase separated out, and the hydrocarbons fractionated into a $C_4^-$ vent gas and a $C_5^+$ liquid product. Each liquid product sample was analyzed by SIMDIS and the chloride content determined by XRF. Groups of samples made under similar conditions were combined and distilled into six fractions with different boiling point ranges. These were: naphtha (<130° C./<275° F.), heavy naphtha (130-200°

C./275-390° F.), jet fuel (200-290° C./390-550° F.), diesel (290-360° C./550-680° F.), neutral base oil (360-500° C./680-930° F.), and bright stock (>500° C./>930° F.). Each fraction was subsequently analyzed, and selected data is summarized in Table I.

TABLE I

| | Run 1 | Run 2 | Run 3 | Run 4 | Run 5 |
|---|---|---|---|---|---|
| Reaction Temperature, ° C. | 10-20 | 10-20 | 10-20 | Adiabatic, 40 | Adiabatic, 35 |
| Olefin Feed | FCC Butenes | FCC Butenes | FCC Butenes | FCC Butenes | FCC Pentenes |
| Iso Feed | Isobutane | Isobutane | Isobutane | Isobutane | Isopentane |
| I/O | 3.5-9 | 2.8-4.2 | 8 | 7.6 | 3.7-4.7 |
| Olefin/HCl, mole/mole | 250-640 | 260-730 | 60 | 60 | 77 |
| Olefin/IL, g/g | 0.3-1.3 | 4.5-26 | 4.3-4.5 | 2.5-5 | 7 |
| Olefin LHSV | 3-7 | 6-19 | 6.1 | 6.6 | 9 |
| Olefin Conversion, wt % | >98 | 60-94 | 99-100 | 99-100 | 100 |
| Wt % Naphtha | 14.5 | 12.0 | 21.4 | 25.8 | 20.5 |
| RON | | | 97.00 | 94.4 | |
| MON | | | 92.00 | | |
| Wt % Heavy Naphtha | 9.5 | 5.7 | 11.3 | 11.5 | 29.9 |
| Bromine Number | 48 | 59 | 12 | 21 | 106 |
| Density, 60° F., g/ml | 0.75 | 0.77 | 0.75 | 0.75 | 0.77 |
| API at 60° F. | 56.0 | 53.0 | 56.6 | 56.2 | 52.9 |
| RON | | 95.9 | | | |
| Smoke Point, mm | 37.00 | 37.00 | 43.00 | 42.00 | 30.00 |
| Flash Point, ° C. | | | 25.00 | 40.00 | 34.00 |
| Cloud Point, ° C. | <−60 | <−60 | <−60 | <−60 | <−60 |
| Freeze Point, ° C. | <−60 | <−60 | <−60 | <−60 | <−60 |
| Viscosity, @-20° C., mm²/s | 2.89 | 2.98 | 3.34 | 3.38 | 2.40 |
| Wt % Jet Fuel | 18.6 | 19.9 | 19.0 | 17.5 | 29.7 |
| Bromine Number | 64 | 70 | 37 | 43 | 82 |
| Density, 60° F., g/ml | 0.80 | 0.80 | 0.79 | 0.80 | 0.81 |
| API at 60° F. | 45.3 | 44.8 | 47.1 | 45.4 | 44.2 |
| Smoke Point, mm | 30.00 | 31.00 | 34.00 | 35.00 | 26.00 |
| Flash Point, ° C. | 97.00 | 87.00 | 93.00 | 87.00 | 88.00 |
| Cloud Point, ° C. | <−60 | <−60 | | <−60 | <−60 |
| Freeze Point, ° C. | <−60 | <−60 | | <−60 | <−60 |
| Viscosity, @-20° C., cP | 29.13 | 21.68 | 25.26 | 17.66 | 19.92 |
| Wt % Diesel | 20.2 | 23.1 | 17.8 | 22.3 | 12.9 |
| Bromine Number | 43 | 58 | 50 | 52 | 71 |
| Density, 60° F., g/ml | 0.82 | 0.82 | 0.82 | 0.82 | 0.83 |
| API at 60° F. | 40.1 | 41.1 | 41.0 | 41.9 | 38.5 |
| Cetane Number | | 25.60 | 25.30 | | |
| Kinematic Viscosity at 40° C., mm²/s | 15.04 | 12.58 | 13.2 | 10.81 | 13.86 |
| Wt % Neutral Base Oil | 30.6 | 37.2 | 29.7 | 20.6 | 5.6 |
| Bromine Number | 38 | 30 | 36 | 38 | 50 |
| Density, 60° F., g/ml | 0.85 | 0.85 | 0.84 | 0.84 | 0.86 |
| API at 60° F. | 34.4 | 35.7 | 0.84 | 0.84 | 0.86 |
| Kinematic Viscosity at 40° C., mm²/s | 124.8 | 155.4 | 164.6 | 120.8 | |
| Kinematic Viscosity at 100° C., mm2/s | 10.1 | 10.8 | 10.8 | 9.1 | |
| VI | 39 | 17 | 4 | 11 | |
| Pour Point, ° C. | −27 | −25 | −21 | −25 | |
| Wt % Bright Stock | 6.6 | 2.1 | 0.8 | 2.2 | 0 |
| Bromine Number | 4 | 9 | | | |
| Density, 60° F., g/ml | 0.92 | 0.91 | 0.98 | | |
| API at 60° F. | 23.0 | 24.8 | 12.4 | | |
| Kinematic Viscosity at 40° C., mm²/s | 19015 | 17195 | | | |
| Kinematic Viscosity at 100° C., mm²/s | 486 | 352 | | | |
| VI | 153 | 122 | | | |
| Pour Point, ° C. | 4 | 6 | | | |
| ΔVI of Neutral Oil and Bright Stock | 114 | 105 | | | |

During runs 1-3 the reaction temperature was controlled by cooling the packed bed contactor with a recirculation cooling medium.

During runs 4 and 5 the packed bed contactor was operated without external cooling, i.e. adiabatically. The packed bed contactor was kept cool by using in-situ evaporation of light components in the effluent. It is notable that even with the removal of light components in the effluent that greater than 98 wt % olefin conversion was achieved.

During the runs with mixed FCC butenes the fixed bed contactor was maintained at 50 psi. Ionic liquid was recycled from the effluent back to the fixed bed contactor at a rate of 0.5 to 1 g/min (0.4 to 0.8 ml/min) with a small make up of fresh ionic liquid (less than 10 wt %). The fresh ionic liquid was added to maintain a fairly constant level of conjunct polymer in the ionic liquid. The feed stream comprising the mixed FCC butenes was flowed to the fixed bed contactor at 5.5 to 6 ml/min. The average residence time for the FCC butenes in the fixed bed contactor was about 30 min. and the average residence time for the ionic liquid in the fixed bed contactor as between about 5 and 10 min. The volumetric ratio of ionic liquid to FCC butenes was about 1:1. One advantage of using the fixed bed contactor was that there was a difference between the average residence times for the hydrocarbon feed and the ionic liquid in the reactor. Thus the feed flows can be varied independently, given an added process optimization handle.

The olefin space velocities during the five different runs varied from 3 to 19 LHSV. These space velocities were much higher, approximately 10 times higher, than what would be needed using a continuously stirred tank reactor. This means that the reactor volume for converting a given olefin stream was considerably smaller, e.g. greater than 5 or 10 times smaller than what would be needed in a CSTR for an equivalent olefin conversion of a given olefin stream.

It is notable that the smoke points of the heavy naphtha and jet products produced in the runs with FCC mixed butenes were high, generally 30 mm or higher.

It is also notable that the bright stocks produced in the fixed bed contactor had VIs that met the requirements for API Group III base oil. They had high kinematic viscosities, 200 mm²/s or higher at 100° C., and VIs of 120 or higher. The yields of bright stock were at least 2 wt % of the total products made in the fixed bed contactor in three of the runs using mixed FCC butenes.

In Run 1 and Run 2 significant amounts of both a lubricant and a bright stock were produced. An unusual feature in these runs was that the difference in the VIs of the lubricant and the bright stock made in a single run was high, for example at least 50, at least 75, at least 85, or at least 100. The conditions during these runs favored the formation of heavy oligomers having desired low levels of branching and favorable placement of the branches in the molecules.

The term "comprising" means including the elements or steps that are identified following that term, but any such elements or steps are not exhaustive, and an embodiment can include other elements or steps. For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

It is claimed:

1. A process for producing liquid hydrocarbon products, comprising:
   (a) introducing an acidic ionic liquid to a reactor comprising a solid support that is a porous particulate having pores up to 200 Å;
   (b) feeding to the reactor a feed stream comprising a Brønsted acid and a hydrocarbon mixture comprising:
      i. at least one alkylatable hydrocarbon, and
      ii. at least one alkylating agent; and
   (c) collecting one or more liquid hydrocarbon products in an effluent from the reactor, wherein the one or more liquid hydrocarbon products are oligomer products made from the alkylatable hydrocarbon; and wherein the one or more liquid hydrocarbon products comprise from 5 wt % to 25.8 wt % hydrocarbons with a boiling point less than 130° C.

2. The process of claim 1, wherein the porous particulate is selected from the group consisting of silica, alumina, Mania, zirconia, thoria, boria, and mixtures thereof.

3. The process of claim 1, wherein the porous particulate is placed in a fixed bed and a pore volume in the reactor is greater than 25 vol % of a total volume of the reactor.

4. The process of claim 1, wherein the Brønsted acid is selected from the group consisting of HCl, HBr, HI, HF, sulfuric acid, and mixtures thereof.

5. The process of claim 1, wherein the solid support is placed in a fixed bed or a fluidized bed and the feed stream is introduced at one end of the reactor and withdrawn at the opposite end of the reactor.

6. The process of claim 1, wherein the at least one alkylating agent comprises an olefin.

7. The process of claim 6, wherein the at least one alkylating agent comprises mixed butenes.

8. The process of claim 1, wherein the at least one alkylatable hydrocarbon is selected from the group consisting of olefins, isoparaffins, branched naphthenes, aromatic hydrocarbons, and mixtures thereof.

9. The process of claim 1, wherein the hydrocarbon mixture comprises a $C_2$-$C_{12}$ olefin and a $C_4$ - $C_{25}$ isoparaffin.

10. The process of claim 1, wherein the one or more liquid hydrocarbon products additionally comprise a middle distillate, a base oil, or a mixture thereof.

11. The process of claim 1, wherein the ionic liquid has a general formula RR'R"NH$^+$Al$_2$Cl$_7^-$, wherein N is a nitrogen containing group, and wherein RR' and R" are alkyl groups containing 1 to 12 carbons, and where RR' and R" may or may not be the same.

12. The process of claim 1, wherein the acidic ionic liquid comprises a cation selected from the group of an alkyl-pyridinium, an alkyl-imidazolium, or a mixture thereof.

13. The process of claim 1, wherein the acidic ionic liquid comprises a strongly Lewis acidic anion.

14. The process of claim 1, wherein a fresh acidic ionic liquid is added continuously to the reactor and a passivated acidic ionic liquid is withdrawn continuously from the reactor.

15. The process of claim 1, wherein a difference between an average residence time for the hydrocarbon mixture and an average residence time for the acidic ionic liquid in the reactor is at least 1 minute.

16. The process of claim 1, wherein a flow of the acidic ionic liquid during introducing of the acidic ionic liquid to the reactor and a flow of the feed stream comprising the hydrocarbon mixture are varied independently.

17. The process of claim 1, wherein the acidic ionic liquid and the one or more liquid hydrocarbon products do not form an emulsion.

18. The process of claim 1, wherein the reactor is operated adiabatically.

19. The process of claim 18, wherein a volatile hydrocarbon from a reaction zone in the reactor evaporates to cool the reactor.

20. The process of claim 18, wherein greater than 98 wt % of the alkylating agent is converted.

21. The process of claim 1, wherein a feed rate of the alkylating agent to the reactor is at least two LHSV.

22. The process of claim 1, wherein the one or more liquid hydrocarbon products comprise a heavy naphtha or a jet fuel having a smoke point of 30 mm or higher.

23. The process of claim 1, wherein the one or more liquid hydrocarbon products comprise a bright stock having a kinematic viscosity at 100° C. of 200 mm$^2$/s or higher and a VI of 80 or higher.

24. The process of claim 1, wherein the one or more liquid hydrocarbon products comprise a bright stock having a VI of 120 or higher.

25. The process of claim 1, wherein increasing the amount of an alpha olefin in the alkylating agent increases a wt % bright stock that is produced.

26. The process of claim 1, wherein the one or more liquid hydrocarbon products in the effluent from the reactor comprise at least 2 wt % hydrocarbons with a boiling point greater than 500° C.

27. The process of claim 1, wherein the one or more liquid hydrocarbon products comprise:
    (a) at least 5 wt % hydrocarbons with a boiling point less than 130° C. and having a RON of 90 or higher, and
    (b) at least 2 wt % hydrocarbons with a boiling point greater than 500° C. and a VI of 100 or higher.

28. The process of claim 1, wherein the one or more liquid hydrocarbon products comprise:
    (a) a lubricant having a kinematic viscosity of 180 mm$^2$/s or less at 40° C. and a VI greater than 15, and
    (b) a bright stock with a VI greater than 100.

29. The process of claim 28, wherein a difference between the VI of the lubricant and the VI of the bright stock is at least 50.

30. A process for producing liquid hydrocarbon products, comprising:
    (a) introducing an acidic ionic liquid to a reactor comprising a solid support that is a porous particulate having pores up to 200 Å;
    (b) feeding to the reactor a feed stream comprising a Brønsted acid and a hydrocarbon mixture;
    (c) cooling the reactor by evaporating, in situ, a volatile hydrocarbon from a reaction zone in the reactor; and
    (d) collecting one or more liquid hydrocarbon products in an effluent from the reactor, wherein the one or more liquid hydrocarbon products are oligomer products, alkylate products, or mixtures thereof, made from the hydrocarbon mixture; and wherein the one or more liquid hydrocarbon products comprise from 5 wt % to 25.8 wt % hydrocarbons with a boiling point less than 130° C.

31. A process for producing liquid hydrocarbon products, comprising:
    (a) introducing an acidic ionic liquid to a reactor comprising a solid support that is a porous particulate having pores up to 200 Å;
    (b) feeding to the reactor a feed stream comprising a Brønsted acid and a hydrocarbon mixture comprising:
        i. at least one alkylatable hydrocarbon, and
        ii. at least one alkylating agent;
    (c) independently varying a flow of the acidic ionic liquid during the introducing and a flow of the feed stream during the feeding; and
    (d) collecting one or more liquid hydrocarbon products in an effluent from the reactor; wherein a fresh acidic ionic liquid is added continuously to the reactor and a passivated acidic ionic liquid is withdrawn continuously from the reactor; wherein the one or more liquid hydrocarbon products are oligomer products, alkylate products, or mixtures thereof, made from the alkylatable hydrocarbon; and wherein the one or more liquid hydrocarbon products comprise a middle distillate, a base oil, or a mixture thereof; and wherein the one or more liquid hydrocarbon products additionally comprise from 5 wt % to 25.8 wt % hydrocarbons with a boiling point less than 130° C.

32. A process for producing liquid hydrocarbon products, comprising:
    (a) introducing an acidic ionic liquid to a reactor comprising a solid support that is a porous particulate having pores up to 200 Å;
    (b) feeding to the reactor a feed stream comprising a Brønsted acid and a hydrocarbon mixture comprising:
        i. at least one alkylatable hydrocarbon, and
        ii. at least one alkylating agent;
    (c) controlling the reactor at a temperature from 10° C. to 35° C.; and
    (d) collecting one or more liquid hydrocarbon products in an effluent from the reactor, wherein the one or more liquid hydrocarbon products are oligomer products, alkylate products, or mixtures thereof, made from the alkylatable hydrocarbon; and wherein the one or more liquid hydrocarbon products comprise from 5 wt % to 25.8 wt % hydrocarbons with a boiling point less than 130° C.

* * * * *